United States Patent
Dorsey et al.

(10) Patent No.: US 7,179,085 B2
(45) Date of Patent: Feb. 20, 2007

(54) APPARATUS FOR DISPENSING DENTAL SOLUTIONS

(75) Inventors: Denis P. Dorsey, Levittown, PA (US); Randall G. Cohen, Yardley, PA (US); Chen-Cheng Kuo, Taipei (TW)

(73) Assignee: Denteque, Langhorne, PA (US)

( * ) Notice: Subject to any disclaimer, the term of this patent is extended or adjusted under 35 U.S.C. 154(b) by 0 days.

(21) Appl. No.: 10/990,136

(22) Filed: Nov. 16, 2004

(65) Prior Publication Data
US 2006/0105292 A1    May 18, 2006

(51) Int. Cl.
*A61C 17/02* (2006.01)
(52) U.S. Cl. .......................................... 433/80
(58) Field of Classification Search ................. 433/80, 433/89, 90; 401/268
See application file for complete search history.

(56) References Cited

U.S. PATENT DOCUMENTS

| | | | |
|---|---|---|---|
| 4,997,371 A | 3/1991 | Fischer | 433/90 |
| 5,217,024 A | 6/1993 | Dorsey et al. | 128/758 |
| 5,246,371 A | 9/1993 | Fischer | 433/217 |
| 5,269,684 A | 12/1993 | Fischer | 433/90 |
| 5,286,257 A | 2/1994 | Fischer | 604/82 |
| 6,390,817 B1 | 5/2002 | Jensen | 433/89 |
| 6,612,465 B2 | 9/2003 | Pierson et al. | 222/82 |
| 6,749,356 B1 | 6/2004 | Mead et al. | 401/289 |
| 2005/0032020 A1* | 2/2005 | Han et al. | 433/80 |

\* cited by examiner

*Primary Examiner*—Cary E. O'Connor
(74) *Attorney, Agent, or Firm*—Russell J. Egan

(57) ABSTRACT

An apparatus for dispensing a dental solution is disclosed and includes a dispensing nozzle adapted for attachment to a syringe. The dispensing nozzle has a curved applicator tip with a securely mounted brush that extends beyond the applicator tip to aid in placement of the dental solution. A retainer hub is positioned in the dispensing nozzle to prevent the brush from retracting into or being expelled from the dispensing nozzle during use.

23 Claims, 2 Drawing Sheets

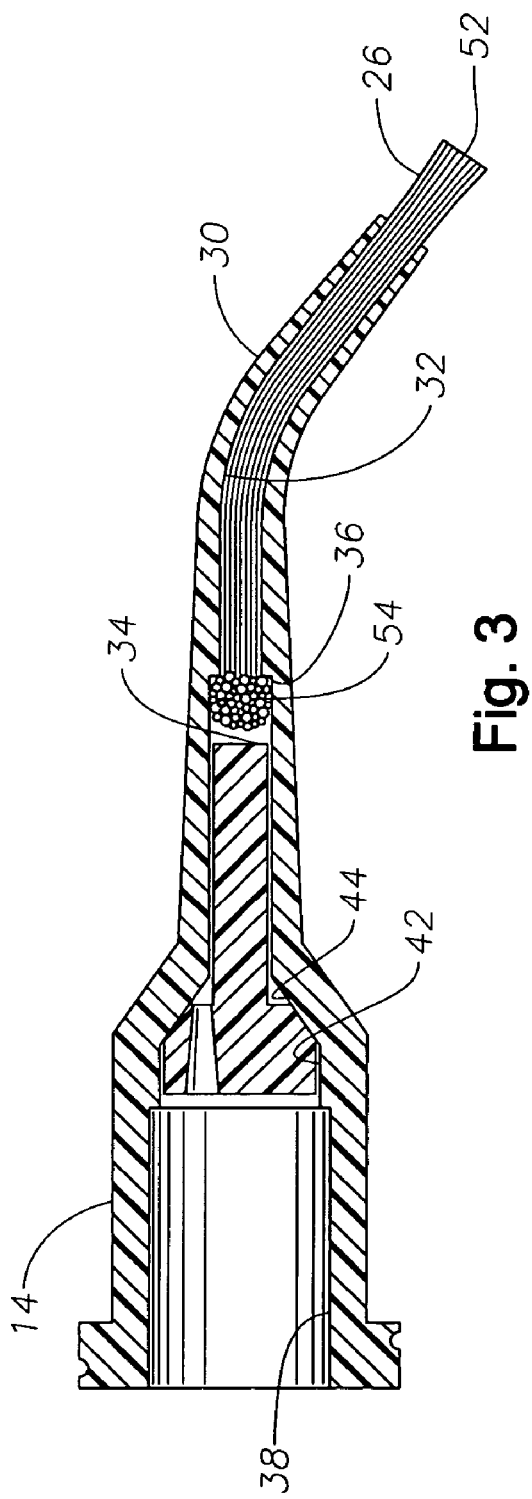
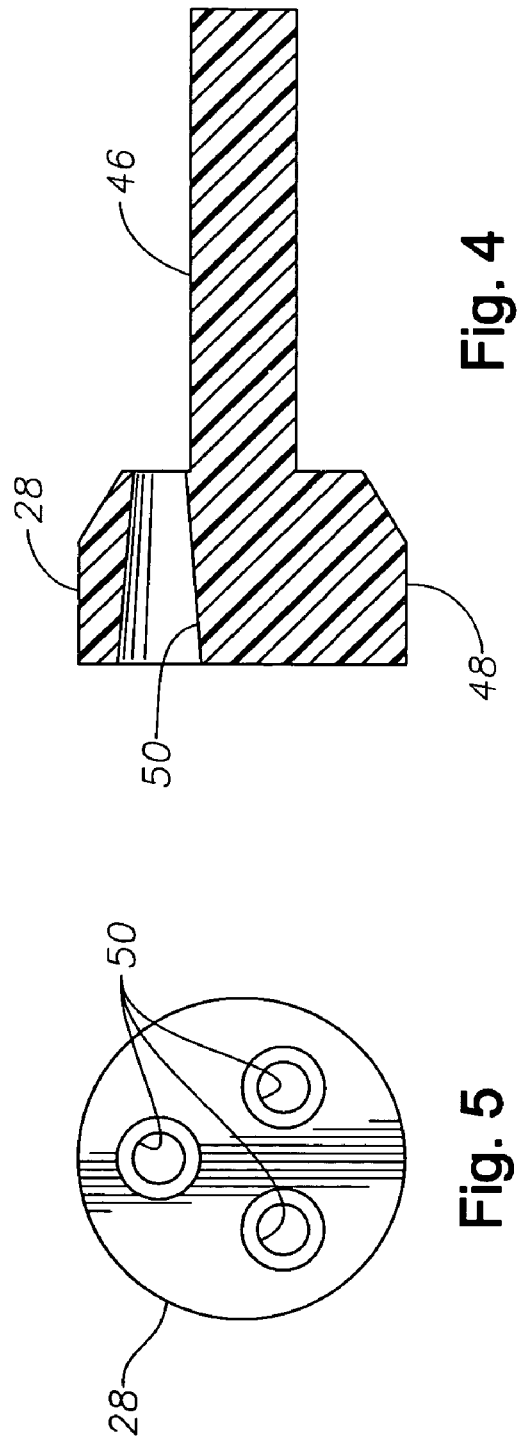
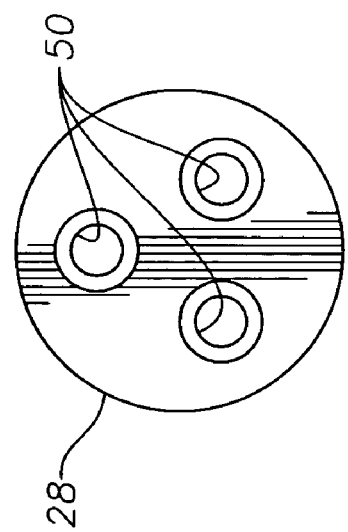

APPARATUS FOR DISPENSING DENTAL SOLUTIONS

BACKGROUND OF THE INVENTION

1. Field of the Invention

This invention relates to an apparatus for dispensing dental solutions such as an anti-plaque mouthwash or medicament to a person's teeth and under gum tissue. The apparatus also could be used by a dentist is dispense a variety of medicaments and disinfectants, or a bonding agent to a person's tooth surface during a dental repair procedure.

The apparatus uses a brush extending from the nozzle or tip of the apparatus to aid in applying or spreading the dental solution being dispensed. In order for such an apparatus to be useful, the brush extending from the nozzle must remain in position during use. If the brush retracts into the nozzle tip during use, the apparatus is useless as the brush is not available to control the spreading of the solution. Similarly, if the brush is expelled from the nozzle tip during use, the apparatus is of no use.

Such an apparatus has a dual function. The apparatus must be able to allow a thinner, i.e., lower viscosity, fluid such as mouthwash to flow through the nozzle tip with the brush not impeding the flow of fluid. In this case, the brush is often used to urge or force the mouthwash into tight spaces around teeth in a "scrubbing" action that tries to force the brush back into the nozzle tip. When the apparatus is used to deliver a thicker, i.e., higher viscosity, fluid such as a dental bonding agent, the nozzle tip must allow the dental bonding agent to be pushed through the nozzle, along the brush, without expelling the brush from the nozzle tip. It is therefore critical that such an apparatus have the brush securely anchored to prevent relative movement while allowing the flow of both lower and higher viscosity fluids or solutions.

2. Description of Related Art

U.S. Pat. No. 4,997,371 to D. E. Fischer shows a dental agent applicator for applying dental bonding agents to tooth surfaces. The dental agent applicator shows a brush inserted into the tip of the dental agent applicator and held in place by crimping the tip.

A tissue sampling device with fin shaped finger tabs to aid in manipulation of the device is shown in U.S. Pat. No. 5,217,024 to D. P. Dorsey et al.

U.S. Pat. No. 5,246,371 to D. E. Fischer presents a method of use of an apparatus for delivering a highly filled thixotropic sealant to teeth. The apparatus shows a brush inserted into the tip of the apparatus and held in place by a helical ridge that is formed in the bore of the tip.

U.S. Pat. No. 5,269,684 to D. E. Fischer claims the apparatus shown in U.S. Pat. No. 5,246,371.

A syringe apparatus with detachable mixing and delivery tip is shown in U.S. Pat. No. 5,286,257 to D. E. Fischer. A syringe with two plungers is used to inject air into the delivery tip and mix the substances to be applied with continued movement of the plungers expelling the mixed substances through the delivery tip.

U.S. Pat. No. 6,390,817 B1 to S. Jensen shows a fiber tipped dental substance applicator that is insertable into a bore of an exit orifice of a syringe. A plurality of pathways are formed on the exterior of the applicator to allow the dental substance to flow out the exit orifice of the syringe to the bristles.

A multi-component mixing, storage and dispensing device for use with a plunger shown in U.S. Pat. No. 6,612,465 B2 to P. R. Pierson et al. discloses a double pronged piston for puncturing a sealed movable piston having twin cavities for holding substances to be mixed at the time of application.

U.S. Pat. No. 6,749,356 B1 to W. T. Mead et al. shows a touch-up coating applicator for remote locations the uses a flexible tube to connect the syringe to the brush applicator assembly.

SUMMARY OF THE INVENTION

The apparatus for delivering dental solutions of the present invention is designed to be used by a home user for applying an anti-plaque mouthwash under the gingival tissues and also can be used by the dental professional in dispensing dental bonding agents or other solutions in dental restoration procedures. The apparatus has a dispensing nozzle for dispensing a dental solution. The dispensing nozzle is adapted for attachment to a receptacle such as a syringe for pushing or urging the solution through the dispensing nozzle. The opposite end of the dispensing nozzle has a curved applicator tip with a bore extending through the applicator tip that communicates with the end attached to a syringe. A brush, composed of a bundle of bristles, is disposed within the dispensing bore and extends beyond the applicator tip with its opposite end secured within the dispensing nozzle. The end of the brush within the dispensing nozzle has an enlarged end formed by heating the bristles that secures the brush within the dispensing nozzle. The apparatus will be available with varying bristle thicknesses which will be determined by its use in either clinical or home use applications. The dispensing nozzle includes a retainer hub positioned therein to prevent the brush from retracting into the dispensing bore of the dispensing nozzle during use. The retainer hub includes a plurality of orifices to allow the dental solution to flow from the syringe, around the retainer hub, through the dispensing bore of the applicator tip to the end of the brush extending beyond the applicator tip.

A principal object of the present invention is to provide an apparatus for dispensing dental solutions of different viscosities that may be used by a home user or a dental professional.

Another object of the present invention is to provide an apparatus for dispensing dental solutions that provides a brush on the end of the apparatus that may be used for spreading lower viscosity solutions without the brush being displaced back into the apparatus.

A further object of the present invention is to provide an apparatus for dispensing dental solutions with a brush on the end that may be used with higher viscosity solutions without expelling the brush from the apparatus.

These with other objects and advantages of the present invention are pointed out with specificness in the claims annexed hereto and form a part of this disclosure. A full and complete understanding of the invention may be had by reference to the accompanying drawings and description of the preferred embodiments.

BRIEF DESCRIPTION OF THE DRAWINGS

These and other objects and advantages of the present invention are set forth below and further made clear by reference to the drawings, wherein:

FIG. 3 is a section view of the dispensing nozzle.

FIG. 4 is a section view of the retainer hub.

FIG. 5 is an end view of the retainer hub.

DESCRIPTION OF THE PREFERRED EMBODIMENT

Figure 1:
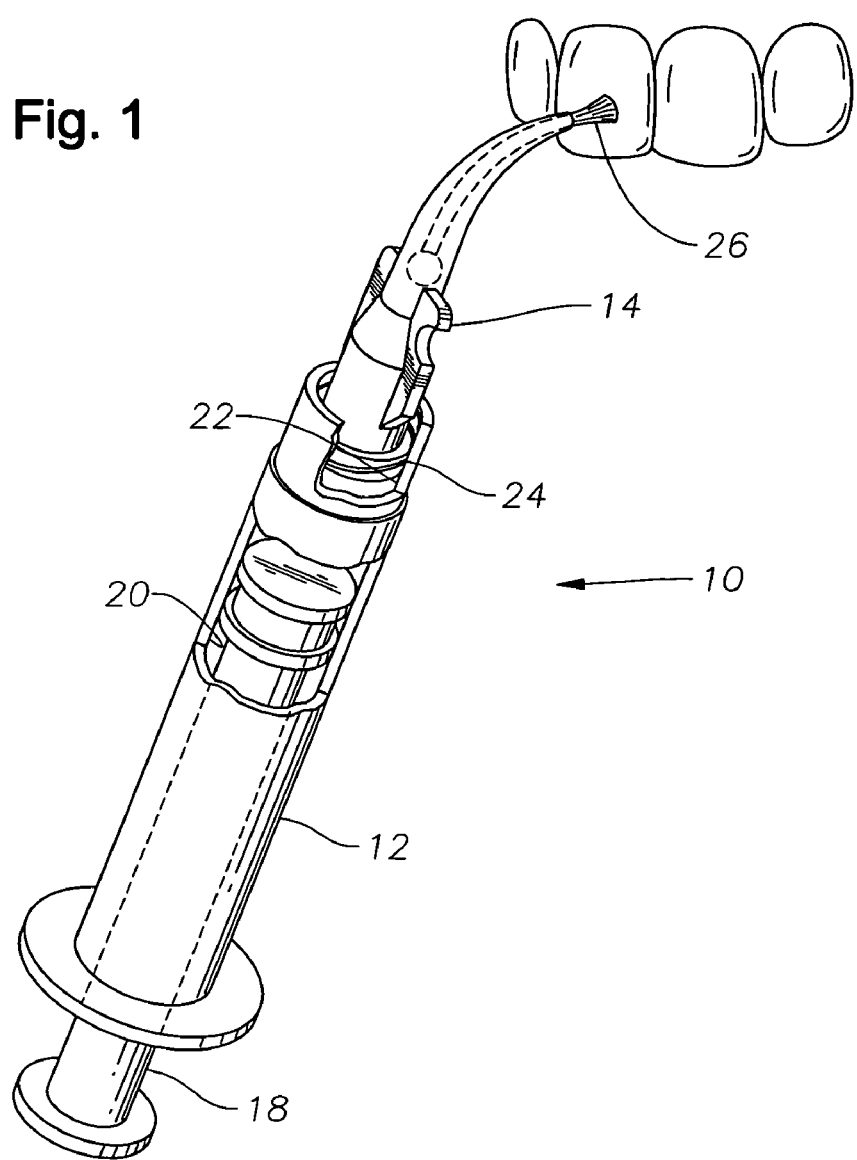
FIG. 1 is a perspective view showing the apparatus for dispensing dental solutions with a syringe attached applying a dental solution to a user's teeth.

With reference to the drawings, and particularly to FIG. 1, a perspective view of an apparatus for delivering dental solutions 10 used in dental restoration or cleaning procedures is shown. The apparatus for delivering dental solutions 10 includes a receptacle means in the form of syringe 12 with nozzle means or dispensing nozzle 14 attached thereto. Syringe 12 has means for controlling delivery of the dental solution from syringe 12 in the form of plunger 18 disposed in central bore 20. Syringe 12 has female luer-lock coupling 22 formed on its distal end that connects to male luer-lock coupling 24 formed on the proximal end of dispensing nozzle 14 in a manner well known to those of ordinary skill in the art to produce a fluid tight connection.

Figure 2:
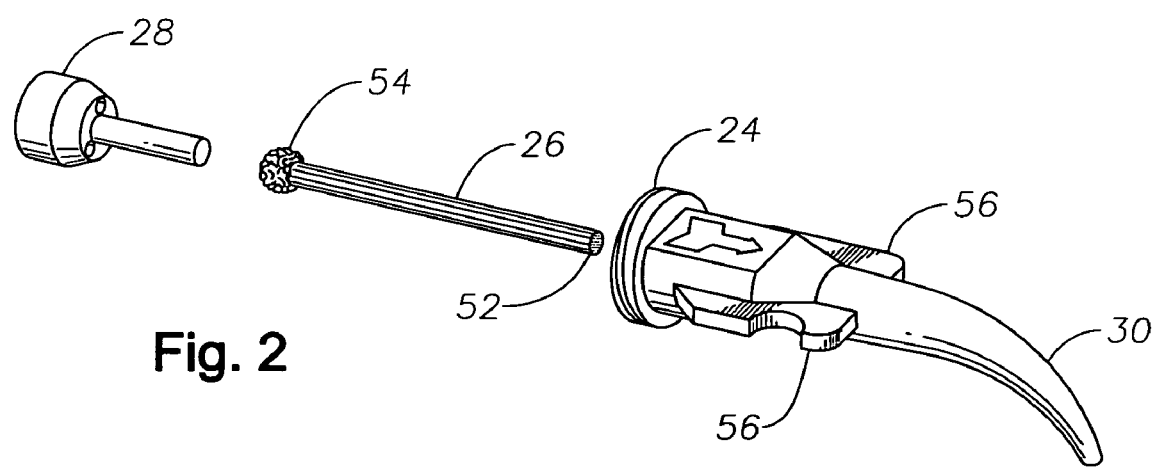
FIG. 2 is an exploded view of the apparatus for dispensing dental solutions.

Dispensing nozzle 14 includes brush 26 extending from its distal end to aid in applying the solution being dispensed. FIG. 2 is an exploded view to aid in understanding the relationship between the parts. Brush 26 extends from the distal end of dispensing nozzle 14 as noted previously. Disposed within dispensing nozzle 14 is retainer means such as retainer hub 28 in a manner to be described hereinafter. Plunger 18 is inserted in syringe 12 to force the solution being dispensed through dispensing nozzle 14 and out through applicator tip 30 formed on the distal end of dispensing nozzle 14. The angle of applicator tip 30 is designed to be very similar to conventional dental instruments to give applicator tip 30 a familiar and comfortable feel to dental professionals.

Referring to FIG. 3, dispensing nozzle 14 is shown in an enlarged sectional view with applicator tip 30 at its distal end. Applicator tip 30 is curved and tapered to aid a user in positioning brush 26 to better control the flow of dental solutions onto the teeth and gums. Brush 26 is disposed in dispensing bore 32 that communicates with the proximal end of dispensing nozzle 14. Dispensing bore 32 extends through applicator tip 30. Dispensing nozzle 14 has intermediate bore 34 centrally located therein having a larger diameter than dispensing bore 32 to form a shoulder 36 therebetween. Adjacent intermediate bore 34 is main bore 38 extending from the proximal end of dispensing nozzle 14 and communicating with intermediate bore 34. Main bore 38 has a larger diameter than intermediate bore 34 to form a shoulder 40 therebetween. Main bore 38 includes reduced diameter 42 and tapered shoulder 44 that transitions to intermediate bore 34. Reduced diameter 42 of main bore 38 receives retainer hub 28 in an interference fit to lock retainer hub 28 in position. Retainer hub 28 is fitted into reduced diameter 42 of main bore 38 under such pressure that excessive pressure applied to the distal end of brush 26 extending from applicator tip 30 cannot dislodge retainer hub 28 from dispensing nozzle 14.

As best seen in FIGS. 4 and 5, retainer hub 28 is of a stepped shoulder design having a first diameter section or prong 46 that extends into intermediate bore 34 adjacent the proximal end of brush 26 and a second diameter section or hub body 48 that is an interference fit in reduced diameter 42 of main bore 38 of dispensing nozzle 14. A plurality of orifices 50 extend through the second diameter section or hub body 48 of retainer hub 28 to allow the solution being dispensed to flow through.

Referring back to FIG. 3, prong 46 of retainer hub 28 is adjacent the proximal end of brush 26. Brush 26 is composed of a plurality of bristles 52 that are sized to substantially fill dispensing bore 32 of applicator tip 30 while allowing the flow of the dental solution through dispensing bore 32 of the applicator tip 30. To ensure brush 26 is not expelled from dispensing bore 32 when dispensing higher viscosity solutions, the proximal end of brush 26 is heated to cause bristles 52 to melt into a larger diameter portion or head 54. When brush 26 is inserted into dispensing nozzle 14 through main bore 38 and intermediate bore 34, head 54 comes to rest on shoulder 36 and is thereby prevented from being expelled during use. While head 54 is sufficiently larger in diameter to be retained on shoulder 36, head 54 is sufficiently porous to allow the dental solution being dispensed to flow therethrough. When dispensing nozzle 14 is being used to dispense a lower viscosity solution such as a anti-plaque mouthwash, a scrubbing action is often used which tries to urge brush 26 back into applicator tip 30. In this instance, prong 46 of retainer hub 28 is adjacent head 54 of brush 26 and resists this movement by virtue of retainer hub 28 being locked in position by its interference fit in dispensing nozzle 14 as previously described. Therefore brush 26 is restrained from movement in either axial direction along dispensing bore 32 of dispensing nozzle 14.

A typical sequence of operation is as follows. When it is desired to dispense a dental solution, syringe 12 is filled from a dispensing bottle (not shown) using plunger 18. The syringe is then connected to dispensing nozzle 14 with luer-lock couplings 22 and 24. A plurality of fin shaped finger tabs 56 are provided on the exterior of dispensing nozzle 14 to aid a user in grasping dispensing nozzle 14 and making the aforementioned luer-lock coupling connection. A user can then hold the assembled apparatus 10 and slowly urge plunger 18 into syringe 12 and dispense the dental solution from syringe 12, through dispensing nozzle 14 and brush 26 and out applicator tip 30. The portion of brush 26 extending from applicator tip 30 can then be used to direct the dental solution onto the teeth or gums, as required.

The construction of our apparatus for dispensing dental solutions will be readily understood from the foregoing description and it will be seen that we have provided an apparatus for dispensing dental solutions of different viscosities that may be used by a home user or a dental professional. Furthermore, while the invention has been shown and described with respect to certain preferred embodiments, it is obvious that equivalent alterations and modifications will occur to others skilled in the art upon the reading and understanding of the specification. The present invention includes all such equivalent alterations and modifications, and is limited only by the scope of the appended claims.

What is claimed is:

1. An apparatus for delivering dental solutions, comprising:

a receptacle means for holding a quantity of a dental solution;

a nozzle means for dispensing said dental solution, said nozzle means having a proximal end in communication with said receptacle means and a dispensing bore extending from said proximal end to a distal end of said nozzle means;

a brush disposed within said dispensing bore of said nozzle means, said brush having a distal end extending beyond said distal end of said nozzle means and a proximal end secured within said nozzle means, said proximal end of said brush having a larger diameter portion that secures said brush within said nozzle means and prevents expulsion of said brush from said nozzle during delivery of said dental solution;

said nozzle means including a retainer means positioned therein to prevent said brush from retracting into said nozzle means during use, said retainer means including at least one orifice to allow flow of said dental solution from said receptacle means through said dispensing bore of said nozzle means to said distal end of said brush extending beyond said distal end of said nozzle means; and plunger means one end of which is received within said receptacle means for controlling delivery of said dental solution form said receptacle means through said nozzle means.

2. An apparatus for delivering dental solutions according to claim 1, wherein:
said nozzle means includes an intermediate bore having a larger diameter than and communicating with said dispensing bore, said intermediate bore containing said larger diameter portion of said brush.

3. An apparatus for delivering dental solutions according to claim 2, wherein:
said nozzle means includes a main bore extending from said proximal end and communicating with said intermediate bore, said main bore having a larger diameter than said intermediate bore.

4. An apparatus for delivering dental solutions according to claim 3, wherein:
said retainer means has a first diameter extending into said intermediate bore of said nozzle means to a position adjacent said larger diameter portion of said brush.

5. An apparatus for delivering dental solutions according to claim 4, wherein:
said retainer means has a second diameter engaging said main bore of said nozzle means with an interference fit to secure said retainer means within said nozzle means.

6. An apparatus for delivering dental solutions according to claim 5, wherein:
said at least one orifice of said retainer means extends through said second diameter of said retainer means.

7. An apparatus for delivering dental solutions according to claim 6, wherein:
said first diameter of said retainer means is smaller than said intermediate bore of said nozzle means to form an annulus to allow the flow of said dental solution from said main bore through said intermediate bore to said dispensing bore of said nozzle means.

8. An apparatus for delivering dental solutions according to claim 7, wherein:
said brush secured within said dispensing bore of said nozzle means comprises a plurality of bristles, said bristles substantially filling said dispensing bore of said nozzle means while allowing the flow of said dental solution through said dispensing bore of said nozzle means.

9. An apparatus for delivering dental solutions according to claim 8, wherein:
said nozzle means is removably secured to said receptacle means.

10. An apparatus for delivering dental solutions according to claim 9, wherein:
said receptacle means is a syringe barrel and said plunger mean is axially moveable within said syringe barrel.

11. An apparatus for delivering dental solutions according to claim 10, wherein:
said nozzle means has a male luer-lock coupling formed at its proximal end for attachment to a mating female luer-lock coupling formed at the distal end of said syringe barrel.

12. An apparatus for delivering dental solutions according to claim 11, wherein:
said nozzle means includes wings formed thereon to aid a user in securing said nozzle means to said syringe barrel.

13. An apparatus for use with a receptacle holding a quantity of a dental solution to aid in controlling delivery of a dental solution to a tooth, comprising:
a receptacle means for holding a quantity of a denial solution;
a dispensing nozzle for dispensing said dental solution, said dispensing nozzle having a proximal end adapted for attachment to said receptacle means, an applicator tip at its distal end with a dispensing bore extending through said applicator tip and said dispensing bore communicating with said proximal end of said dispensing nozzle;
a brush disposed within said dispensing bore, said brash having a distal end extending beyond said applicator tip of said dispensing nozzle and a proximal end secured within said dispensing nozzle, said proximal end of said brush having a larger diameter portion that secures said brush within said dispensing nozzle and prevents expulsion of said brush from said applicator tip during delivery of said dental solution;
said dispensing nozzle including a retainer hub positioned therein to prevent said brush from retracting into said dispensing bore of said dispensing nozzle during use, said retainer hub including at least one orifice to allow flow of said dental solution from said receptacle through said dispensing bore of said applicator tip to said distal end of said brush extending beyond said applicator tip of said dispensing nozzle; and
plunger means receivable within said receptacle means for controlling delivery of said dental solution from said receptacle means through said nozzle means.

14. An apparatus for use with a receptacle holding a quantity of a dental solution to aid in controlling delivery of a dental solution to a tooth according to claim 13, wherein:
said dispensing nozzle includes an intermediate bore having a larger diameter than and communicating with said dispensing bore, said intermediate bore containing said larger diameter portion of said brush.

15. An apparatus for use with a receptacle holding a quantity of a dental solution to aid in controlling delivery of a dental solution to a tooth according to claim 14, wherein:
said dispensing nozzle includes a main bore extending from said proximal end and communicating with said intermediate bore, said main bore having a larger diameter than said intermediate bore.

16. An apparatus for use with a receptacle holding a quantity of a dental solution to aid in controlling delivery of a dental solution to a tooth according to claim 15, wherein:
said retainer hub has a first diameter extending into said intermediate bore of said dispensing nozzle to a position adjacent said larger diameter portion of said brush.

17. An apparatus for use with a receptacle holding a quantity of a dental solution to aid in controlling delivery of a dental solution to a tooth according to claim 16, wherein:

said retainer hub has a second diameter engaging said main bore of said dispensing nozzle with an interference fit to secure said retainer hub within said dispensing nozzle.

18. An apparatus for use with a receptacle holding a quantity of a dental solution to aid in controlling delivery of a dental solution to a tooth according to claim 17, wherein:
said at least one orifice of said retainer hub extends through said second diameter of said retainer hub.

19. An apparatus for use with a receptacle holding a quantity of a dental solution to aid in controlling delivery of a dental solution to a tooth according to claim 18, wherein:
said first diameter of said retainer hub is smaller than said intermediate bore of said dispensing nozzle to form an annulus to allow the flow of said dental solution from said main bore through said intermediate bore to said dispensing bore of said dispensing nozzle.

20. An apparatus for use with a receptacle holding a quantity of a dental solution to aid in controlling delivery of a dental solution to a tooth according to claim 19, wherein:
said brush secured within said dispensing bore of said applicator tip comprises a plurality of bristles, said bristles substantially filling said dispensing bore of said applicator tip while allowing the flow of said dental solution through said dispensing bore of said applicator tip.

21. An apparatus for use with a receptacle holding a quantity of a dental solution to aid in controlling delivery of a dental solution to a tooth according to claim 20, wherein:
said dispensing nozzle has a male luer-lock coupling formed at its proximal end for attachment to said receptacle.

22. An apparatus for use with a receptacle holding a quantity of a dental solution to aid in controlling delivery of a dental solution to a tooth according to claim 21, wherein:
said applicator tip is curved to facilitate application of said dental solution to a tooth.

23. An apparatus for use with a receptacle holding a quantity of a dental solution to aid in controlling delivery of a dental solution to a tooth according to claim 22, wherein:
said dispenser nozzle includes wings formed thereon to aid a user in securing said dispenser nozzle to said receptacle.

* * * * *